(12) United States Patent
Zehnder (10) Patent No.: US 8,162,986 B2
(45) Date of Patent: Apr. 24, 2012

(54) VERTEBRAL COLUMN IMPLANT

(75) Inventor: Thomas Zehnder, Bäch (CH)

(73) Assignee: Spinelab AG, Winterthur (CH)

( * ) Notice: Subject to any disclaimer, the term of this patent is extended or adjusted under 35 U.S.C. 154(b) by 396 days.

(21) Appl. No.: 11/976,138

(22) Filed: Oct. 22, 2007

(65) Prior Publication Data

US 2008/0058812 A1    Mar. 6, 2008

(51) Int. Cl.
*A61B 17/70* (2006.01)
(52) U.S. Cl. .......... 606/260; 606/257
(58) Field of Classification Search .......... 606/60, 606/264–279, 300–320
See application file for complete search history.

(56) References Cited

U.S. PATENT DOCUMENTS

| | | | | |
|---|---|---|---|---|
| 5,536,268 A * | 7/1996 | Griss | | 606/254 |
| 7,125,410 B2 * | 10/2006 | Freudiger | | 606/254 |
| 2003/0220642 A1 * | 11/2003 | Freudiger | | 606/61 |
| 2005/0096659 A1 * | 5/2005 | Freudiger | | 606/73 |
| 2005/0203517 A1 * | 9/2005 | Jahng et al. | | 606/61 |
| 2005/0277932 A1 * | 12/2005 | Farris | | 606/61 |
| 2006/0041259 A1 | 2/2006 | Paul et al. | | 606/61 |
| 2006/0142758 A1 | 6/2006 | Petit | | 606/61 |
| 2007/0005063 A1 * | 1/2007 | Bruneau et al. | | 606/61 |
| 2008/0215095 A1 * | 9/2008 | Biedermann et al. | | 606/246 |

FOREIGN PATENT DOCUMENTS

| | | |
|---|---|---|
| WO | 2004/105577 | 12/2004 |
| WO | 2005/039454 | 5/2005 |
| WO | 2006/066685 | 6/2006 |

* cited by examiner

*Primary Examiner* — Eduardo C Robert
*Assistant Examiner* — Lynnsy Schneider
(74) *Attorney, Agent, or Firm* — Jacobson Holman PLLC (57) ABSTRACT

A vertebral column implant includes a connecting element, which is insertable in the vertebral bodies of a vertebral column via several bone screws. The screws are each provided with a head part for receiving the connecting element, by means of which a firm connection is achievable between bone screws and connecting element. The connecting element is composed of rigid sections and elastic sections. The rigid sections are connectable to the elastic sections via connecting devices. The connecting devices are designed such that the rigid sections and the elastic sections, in each case connected to one another, are aligned substantially coaxially, and their connection is form-fitting.

5 Claims, 12 Drawing Sheets

VERTEBRAL COLUMN IMPLANT

This invention relates to a vertebral column implant, comprising a connecting element and a multiplicity of bone screws, which are screwable into the vertebral bodies of the vertebral column and which are each provided with a head part for receiving the connecting element, with which head parts a firm connection is achievable between bone screw and connecting element, and the connecting element is able to be put together from rigid sections and elastic sections.

Vertebral column implants are known in the state of the art in diverse ways. One hereby distinguishes between two types of systems, namely stabilizing systems consisting of a rigid connecting element, which have as their goal a stiffening of the respective vertebral column, and elastic systems, with which a supporting stabilization of the vertebral bodies is achieved, a certain flexibility between the individual vertebral bodies being desired and allowed.

Rigid stabilization systems, which are known in a manifold way, have, as already mentioned, the goal that problematic vertebral bodies receive a stiffening, so that an osseous growing together of the affected vertebral bodies is achieved. In order to achieve an optimal stabilization, adjacent healthy vertebral bodies must also be included, in addition to the problematic vertebral bodies, which can result in the stiffening taking place over too great an area. Moreover it has often been noted that with the transition from stabilized to no longer stabilized vertebral bodies the load of the vertebral column is too great, so that at this transition point there can be damage as a result of too great a load on the adjacent vertebral bodies.

As has already been mentioned, through the known elastic systems, the vertebrae are stabilized in a supporting way, a certain flexibility between the vertebral bodies being desired and facilitated, however. This system has the drawback, however, that for greatly affected vertebral bodies, in which a stiffening would be desired, a stiffening cannot be attained with these elastic systems; an osseous growing together of the affected vertebral bodies cannot be achieved.

Known from US 2006/0142758 A1 is a combined system, in which elastic and rigid stabilization regions are used. Used here as the elastic stabilization element is a helical spring-synthetic material combination. This elastic stabilization element is connected to the screws via a pure clamping connection.

The object of the present invention is to create a vertebral column implant, with which it is possible to achieve regionally a rigid stabilization of the vertebral column, while in the bordering area the vertebral bodies are supported and stabilized through an elastic system, without a stiffening taking place, and which makes it possible in an optimal and simple way to connect the rigid and elastic elements.

This object is achieved according to the invention in that the rigid sections are connectable to the elastic sections via connecting devices, and the connecting devices are designed such that the rigid sections and elastic sections connected together in each case are aligned substantially coaxially, and the connection is form-fitting.

Created with this design of the invention is a modular system, in which the possibility exists of stabilizing adjacent vertebral bodies rigidly, while further adjacent vertebral bodies are elastically supported and stabilized, a limited possibility of movement being allowed. One thereby has diverse possibilities of stabilizing the vertebral column regionally in an elastic or rigid way, without the intervention on the patient becoming more complex. Thus achieved can be, for example, that the transition phase from rigidly stabilized vertebral bodies to the vertebral bodies no longer to be stabilized can be designed with more care via an elastically stabilized region in the transition area. At least a partial load relief of the affected vertebral bodies can thus be achieved in the area of transition from the rigidly stabilized vertebral bodies to the no longer stabilized vertebral bodies. With this modular vertebral column implant, optimally adapted solutions in each individual case thus result in which the connections between the rigid sections and the elastic sections are optimal through form-locking.

Since the connecting devices are designed such that the rigid sections and the elastic sections connected together in each case are aligned substantially coaxially, great advantages and simplification result during insertion of implants assembled from such rigid and elastic sections.

The rigid sections are preferably made of a metal alloy, in particular a titanium alloy, which results in an optimal tolerance in the patients treated with such implants.

The elastic sections are preferably made of a biocompatible synthetic material, in particular based on polyurethane, whereby the surface can be provided with encircling ribs and grooves.

A further preferred embodiment of the invention consists in that the connecting devices are formed by a U-shaped bow made of a rigid material, which connecting devices have at the bottom of the bow and along the inner side of the legs grooves and ribs corresponding to the ribs and grooves of the elastic sections. Through the co-operation of the ribs and grooves in the connecting device of the elastic section and of the U-shaped bow a firm, form-fitting connection is obtained. A pressing of the elastic section, which would be necessary with a clamping connection, and which could lead to a viscoelasticity of the elastic section, can thereby be avoided.

Preferably the U-shaped bow with the inserted elastic section is lockable with a locking piece which is insertable between the legs of the bow and is held via engagement means. A very simple procedure is thereby obtained for insertion and holding of the elastic section in the U-shaped bow, which can have a positive effect on the duration of the operative intervention.

Another preferred embodiment of the invention consists in that the locking piece has on the side facing the section ribs and grooves that correspond to the ribs and grooves of the elastic section when the locking piece is in the inserted state. Thus the locking piece also contributes to the form-fitting connection between the elastic section and the U-shaped bow in an optimal way.

The connecting devices are preferably attached in each case at an end of a rigid section or at the head part of a screw. An optimal configuration of these connecting devices results therefrom. The connecting together of the different sections can take place in an optimal way.

A connecting element can also be prefabricated, and can be made up of at lest one rigid and at least one elastic section. Preferably the respective connecting device then includes at the rigid section a coaxial bore whose inner walling is provided with projections, in which bore the elastic element is insertable in the production process through casting or injection molding, whereby a form-fitting connection is obtained. The projections here can have different designs.

A further preferred embodiment of the invention consists in that the head parts of the screws are separate from the screws, and have a receiving region for receiving a screw, which screw with the head part of the screw is attachable via a clamping screw, with which clamping screw the rigid section is able to be fixed in the head part of the screw. In this way the screws can first be inserted in the vertebral bodies, and the head part, in which the sections are able to be held, can be subsequently aligned with respect to the screw and the connecting element.

Preferably the receiving region of the head part of the screw has the shape of a spherical recess for receiving a screw, and the upper portion of the screw is designed as a spherical head. In this way the head part allows itself to be optimally aligned in relation to the screw and to be adapted to the sections to be received therein.

Embodiments of the invention will be explained more closely in the following, by way of example, with reference to the attached drawing.

FIG. 5a shows in a three-dimensional representation a connecting device which is installed on the head part for a screw;

FIG. 5b is a sectional representation of the connecting device according to FIG. 5a;

Figure 1:
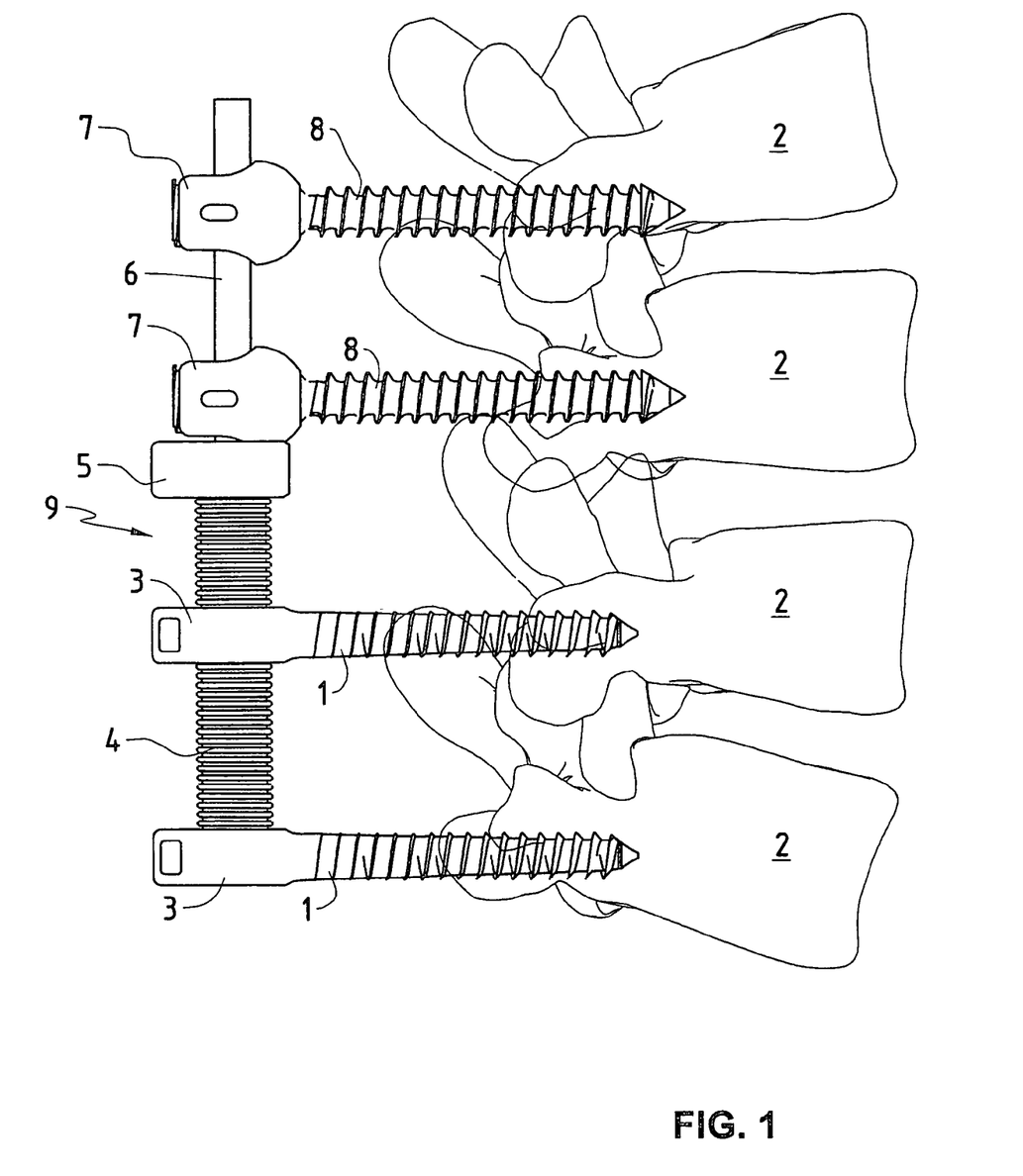
FIG. 1 shows in a schematic representation (not to scale) a vertical column implant inserted in the vertical column with a connecting element, which implant is made up of a rigid section and an elastic section.

As can be seen from FIG. 1, first screws 1 are screwed into vertebral bodies 2. These first screws 1 each bear a first head part 3, which head parts are designed for receiving an elastic section 4, which will still be described in detail later. The one end region of the elastic section 4 is inserted in a connecting device 5, which connecting device 5 is attached to a rigid section 6, as will also be described in detail later. This rigid section 6 is held in second head parts 7, which are installed on second screws 8, which are likewise screwed into the vertebral bodies 2. The elastic section 4 and the rigid section 6 form together the connecting element 9, with which a portion of a vertebral column can be stabilized, with the aid of screws 1 and 8.

Figure 2:
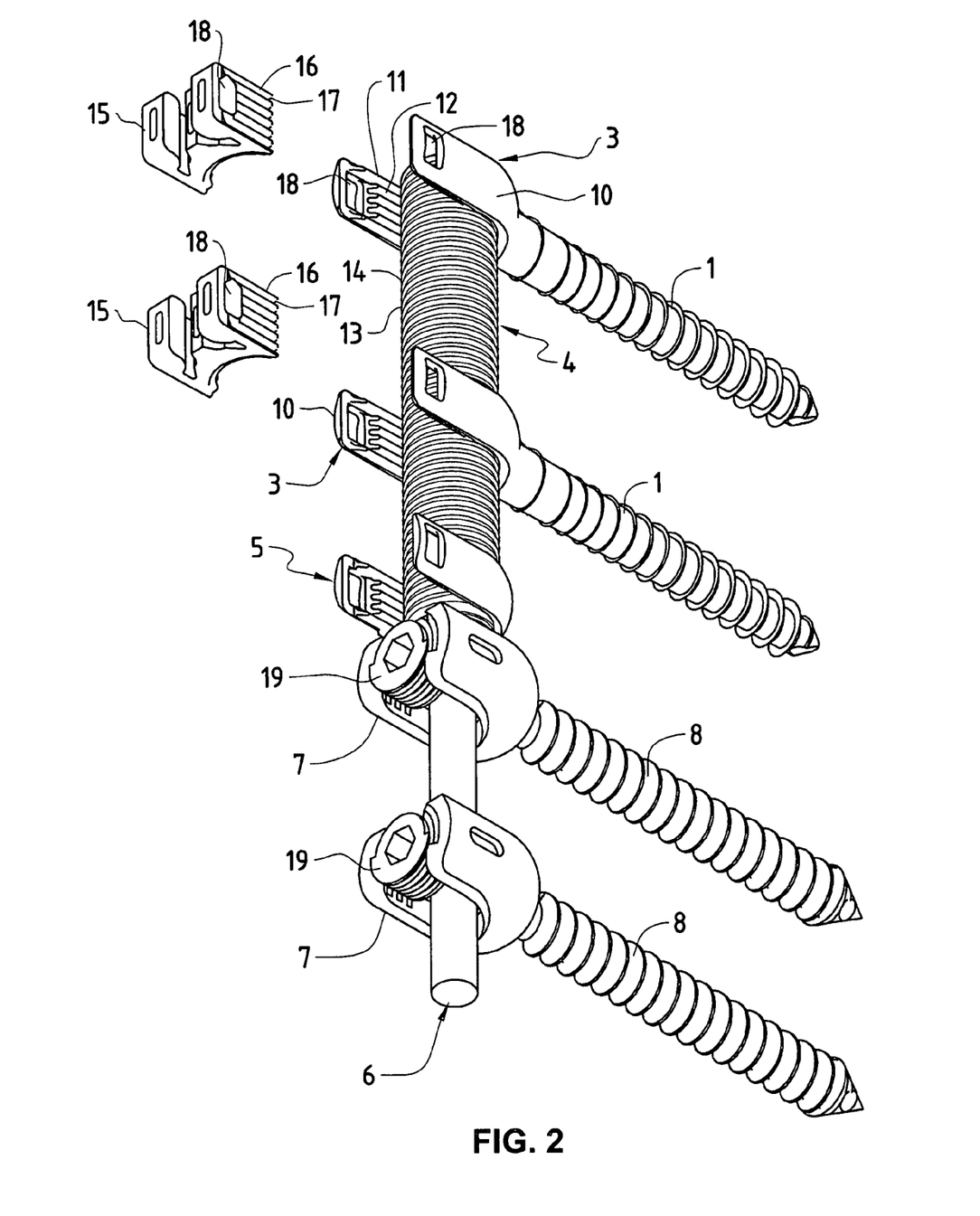
FIG. 2 shows in a three-dimensional representation the vertebral column implant, as shown in FIG. 1.

FIG. 2 shows first screws 1 with first head parts 3 and second screws 8 with second head parts 7. The first head parts 3 are each formed by a U-shaped bow 10 whose inner sides are provided with ribs 11 and grooves 12. The elastic section 4 is likewise provided with encircling ribs 13 and grooves 14. The elastic section 4 is inserted in each case in the U-shaped bow 10, the ribs 11 and grooves 12 of the U-shaped bow 10 engaging in each case in the ribs 13 and grooves 14 of the elastic section 4 in a form-fitting way. The respective U-shaped bow 10 is then locked with a locking piece 15, the locking pieces 15 being likewise provided with ribs 16 and grooves 17 in the area facing the elastic section 4 and on the sides, so that these locking pieces 15 also form a form-fitting connection with the elastic section 4 and the U-shaped bow 10. The locking piece 15 can be held in the respective U-shaped bow 10 by a locking means 18. Such screws with the elastic section and the locking pieces are described, for example, in the European patent application EP-A-1 527 742.

The second head parts 7 of the second screws 8 are likewise designed bow-shaped, so that a rigid section 6 can also be inserted in these second head parts 7 of the second screw 8. This rigid section 6 will be held in a known way via clamping screws 19 in the second head parts 7 of the second screws 8.

Attached to the rigid section 6 is the connecting device 5, with which the rigid section 6 and the elastic section 4 are able to be connected together.

This rigid section 6 and the elastic section 4 could also be joined together to form a pre-assembled connecting element 9 and in this pre-assembled state be inserted and fixed in the head parts 3 and 7 of the screws 1 and 8 already screwed into the vertebral bodies.

Figure 3:
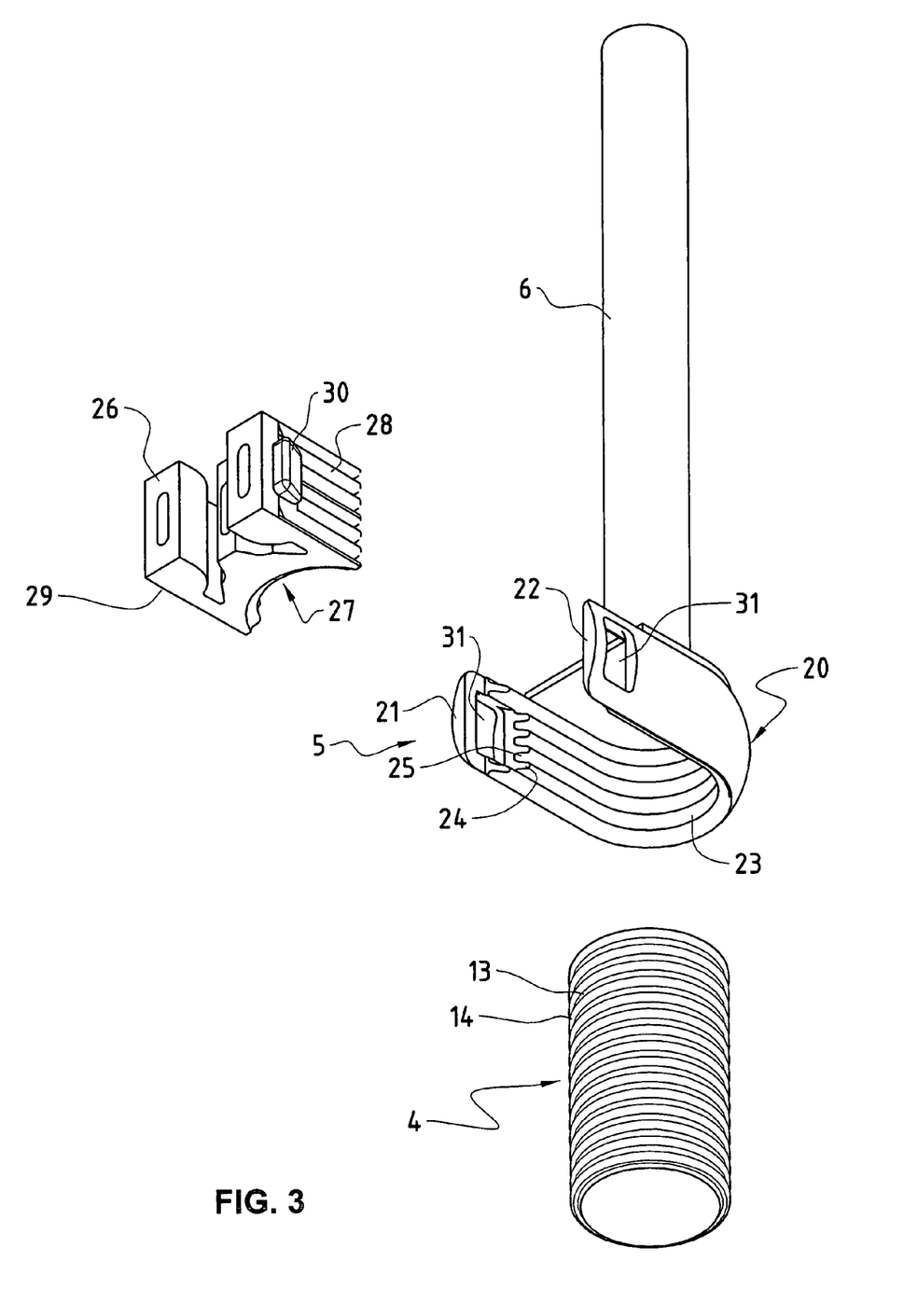
FIG. 3 shows in a three-dimensional representation a view of a connecting device.

Shown in FIG. 3 is the connecting device 5. For this purpose, a U-shaped bow 20 is formed on the end of a rigid section 6. This U-shaped bow is provided with two legs 21 and 22. Ribs 24 and grooves 25 are made at the bottom 23 of this U-shaped bow 20 and along the inner side of the legs 21 and 22. An end region of the elastic section 4 can then be inserted in this U-shaped bow 20. The ribs 24 and grooves 25 of the U-shaped bow 20 then engage in the corresponding ribs 13 and grooves 14 of the elastic section 4. A form-fitting connection is thereby obtained. The elastic section 4 and the rigid section 6 in the connected state are coaxially aligned.

The U-shaped bow 20 can be locked by means of a locking piece 26. The U-shaped bow 20 is designed the same way here as the U-shaped bow 10 of the first screw 1, as can be seen in FIG. 2; the locking piece 26 thus corresponds to the locking piece 15 (likewise FIG. 2). The locking piece 26 also has ribs and grooves on the region 27 facing the elastic section. In addition, corresponding ribs and grooves are also provided on the sides 28 and 29 of the locking piece 26. Thus, in the state of being inserted in the U-shaped bow 20, the locking piece 26 is connected to the U-shaped bow 20 in a form-fitting way via the grooved sides 28 and 29. A form fit also occurs in the region 27, and, to be more precise, with the elastic section 4. The locking piece 26 is held in the U-shaped bow 20 via engagement means 30.

The rigid section 6 and the U-shaped bow 20 attached thereto are made of a metal alloy, in particular a titanium alloy. The elastic section is made up of a biocompatible synthetic material based on polyurethane, whereby it has the desired flexibility. The locking piece 26 is also made of the same material, whereby, for engagement in the U-shaped bow 20, the regions bearing the engagement 30 are elastically deformable, and the engagement means 30 are able to engage in the corresponding recesses 31 of the U-shaped bow 20.

Figure 4:
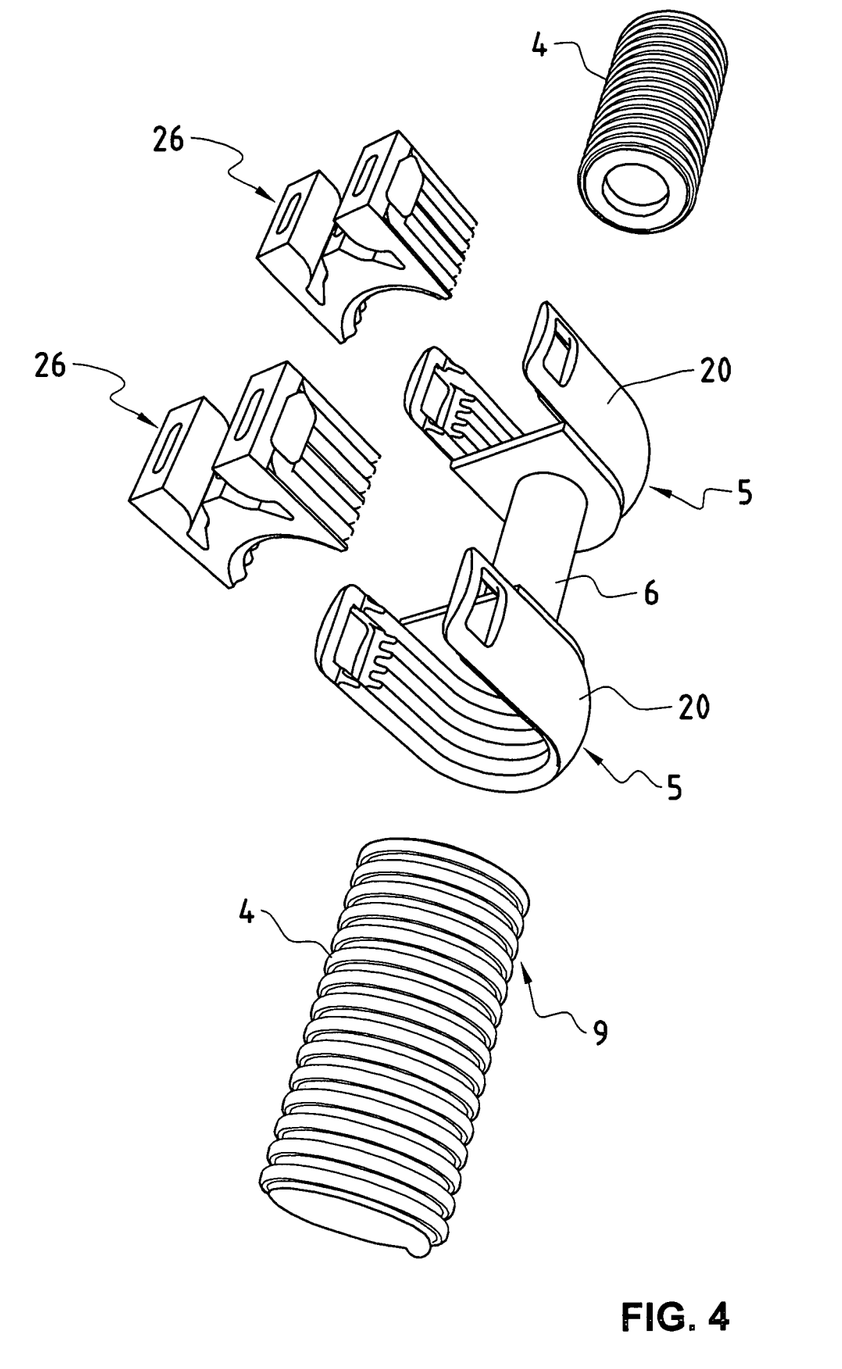
FIG. 4 shows in a three-dimensional representation a view of further connecting devices.

FIG. 4 shows a rigid section 6, on whose two end areas one connecting device 5 each is attached, as described in reference to FIG. 3. An elastic section 4 can be inserted in the U-shaped bow 20 in each case, and can be held with the locking piece 26. Thus a connecting element 9, different when compared to the connecting element 9 shown in FIG. 3, can be obtained. The rigid section 6 is held by second screws 8, while the elastic sections 4 can be held by first screws 1 (FIG. 2). By means of this configuration, two vertebral bodies, for example, could be rigidly stabilized via the rigid section 6 and the corresponding second screws 8; the adjacent vertebral bodies, in which the first screws 1 are inserted, can be elastically stabilized.

Figures 5A, 5B:
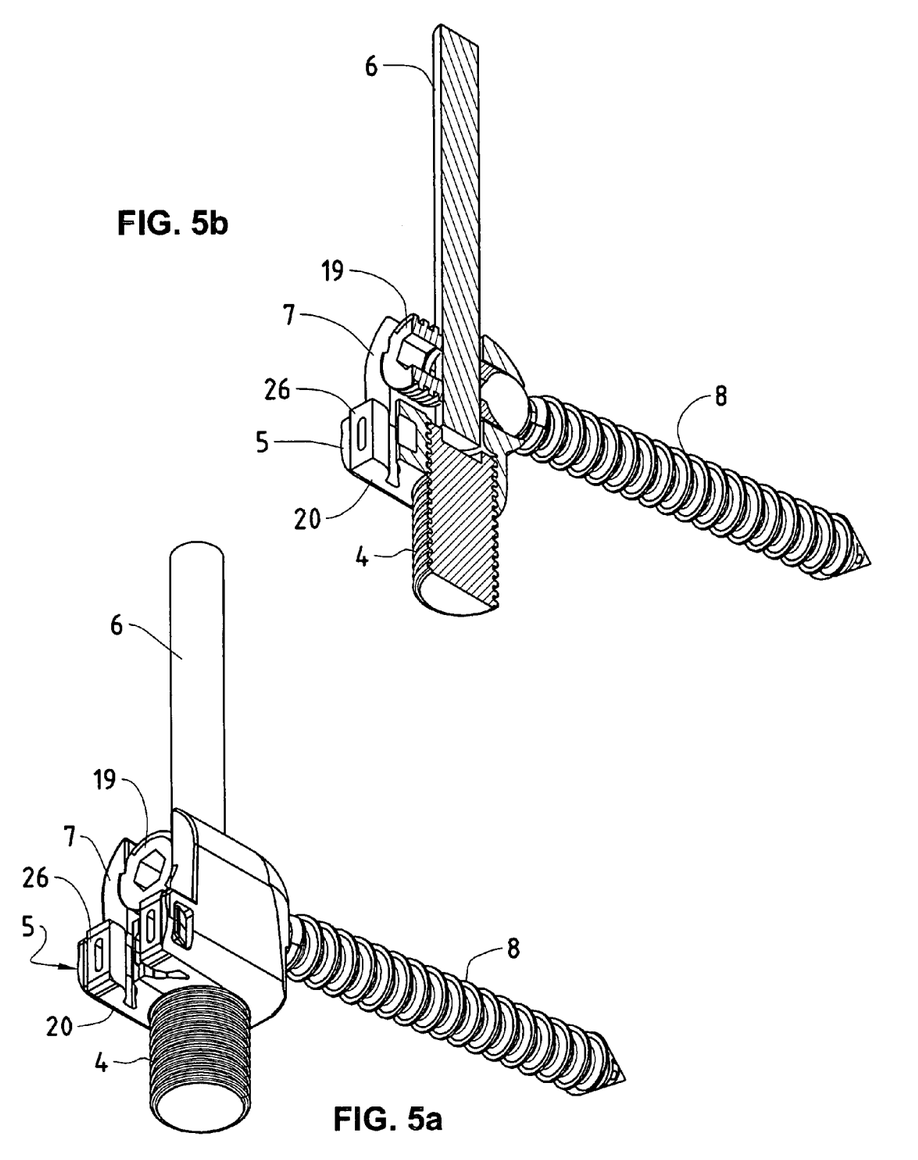

FIGS. 5a and 5b show a connecting device 5, which is attached on the second head part 7 of a second screw 8. Here, too, the connecting device 5 is configured in a way identical to that described with reference to FIG. 3, with the exception that the U-shaped bow 20 is not attached to the rigid section 6, but instead to the second head part 7 of the second screw 8. As has already been mentioned, the rigid section 6 is held in the second head part 7 of the second screw 8 via the clamping screw 19. The elastic section 4 is held in the U-shaped bow 20 of the connecting device 5, this U-shaped bow 20 being once again locked with a locking piece 26.

Figure 6:
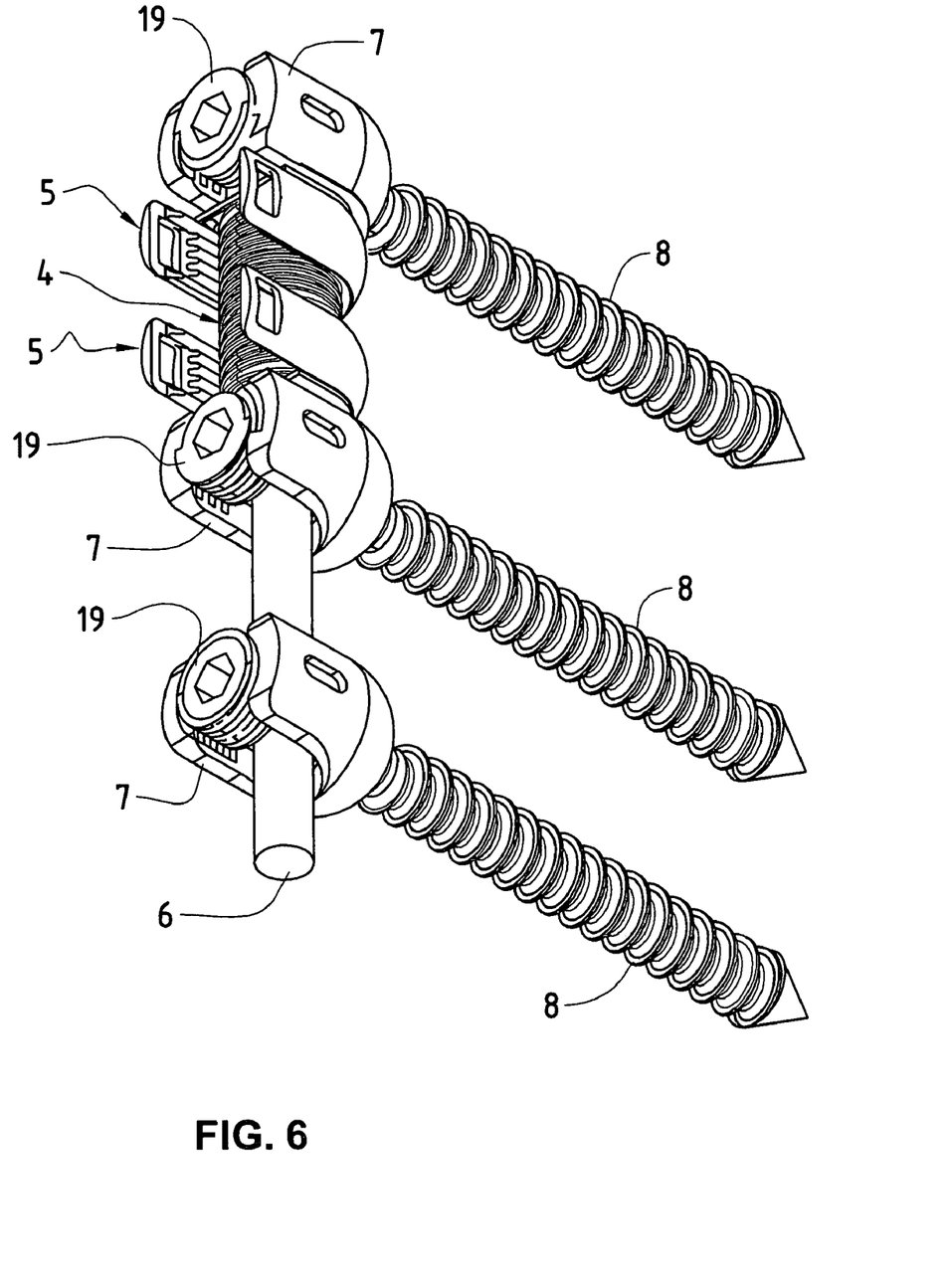
FIG. 6 shows in a three-dimensional representation another configuration of a possibility for a vertebral column implant.

FIG. 6 shows in an application example three second screws 8 with second head parts 7. Inserted in the second head parts 7 of the two second screws 8 shown below in FIG. 6 is a rigid section 6, which is held in the second head parts 7 by the corresponding clamping screws 19. Inserted in the second head part 7 of the second screw 8 shown above is likewise a short rigid section 6, which is not visible in this FIG. 6, and which is held by the clamping screw 19. The two rigid sections 6 are provided on the ends facing each other with a connecting device 5 in each case, as these are described with reference to FIG. 3. The two second screws 8 shown below are rigidly connected to each other via the rigid section 6, and would stabilize in a fixed way the corresponding vertebral bodies. The two second screws 8 shown above are connected to each other via an elastic section 4; the corresponding vertebrae would hereby be elastically stabilized.

It would also be conceivable to use such second head parts 7, provided with connecting devices 5, as are shown and correspondingly described in FIGS. 5a and 5b, instead of the two second head parts 7 shown above.

The connecting element seen and shown from the bottom up in FIG. 6, which is made up of a rigid section 6, an elastic section 4, and again a rigid section 6, could also be pre-assembled, and be inserted in this pre-assembled state in the second screws already screwed into the vertebral bodies.

Figure 7:
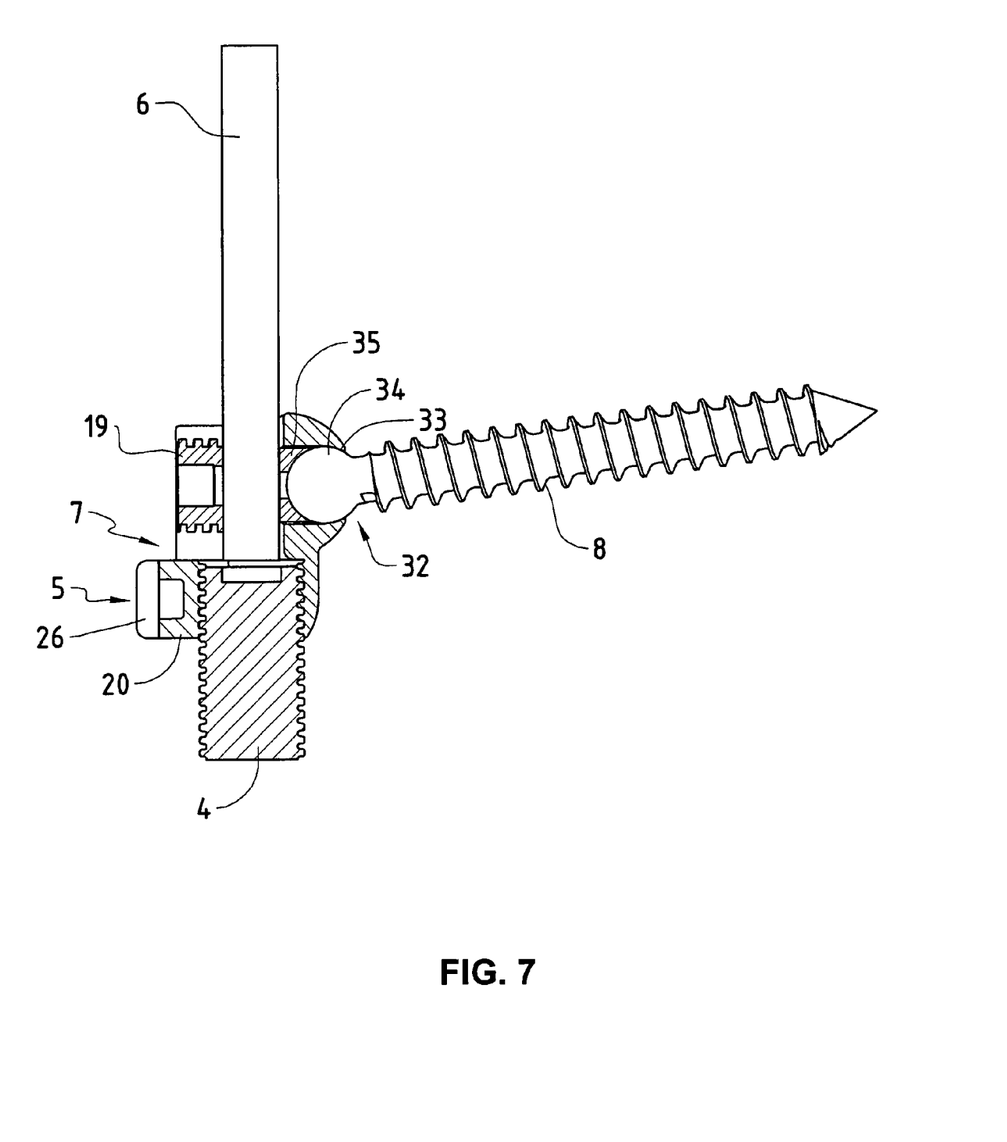
FIG. 7 is a sectional representation of a screw with head part put on, a connecting device being installed at the head part.
Figure 8:
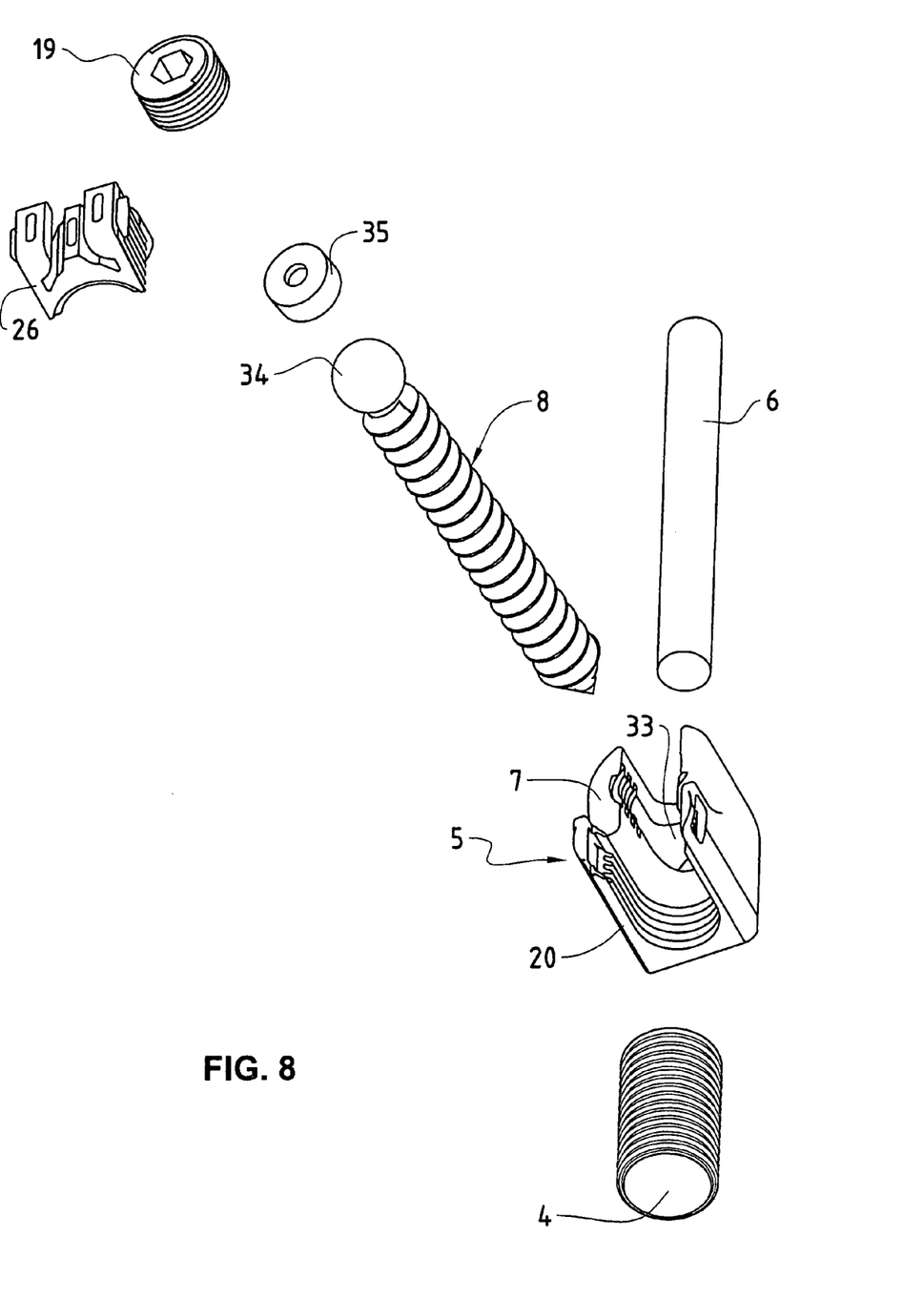
FIG. 8 shows in a disassembled, three-dimensional representation a screw with head part and connecting device installed on this head part.

The two FIGS. 7 and 8 show a second screw 8 with a second head part 7, to which head part 7 is attached a U-shaped bow 20 of a connecting device 5. The screw 8 is separate from the head part 7. The head part 7 has a receiving region 32, which has the shape of a spherical recess 33. The second screw 8 is provided with a spherical head 34. The second screw 8 can now be inserted in the second head part 7 in such a way that the spherical head 34 of the second screw 8 comes to lie in the spherical recess 33 of the second head part. An insert piece 35 is then inserted on the spherical head 34. The rigid section 6 can now be inserted in the second head part 7 of the second screw 8. This rigid section 6 is then pressed against the insert piece 35 via the clamping screw 19, which pressing is passed on to the spherical head 34 of the second screw 8, and this spherical head 34 is then fixed in the spherical recess 33. Thereby obtained in a second head part movable in relation to the second screw 8, which in the inserted and fixed state, however, no longer allows any movement mutually. The second head part 7 and thus the rigid section 6 can thereby be adjusted and then fixed in relation to the second screw 8. The elastic section 4 can then be inserted in den U-shaped bow 20, as already described in the preceding, and can be fixed via the locking piece 26.

Parts of a connecting element or a whole connecting element can also be pre-assembled, consisting of rigid sections and elastic sections, which are then insertable in the bone screws screwed into the vertebral bodies. The rigid sections and the elastic sections are hereby firmly connected together, as will still be described in the following. Correspondingly designed portions of a connecting element can be connected to each other or to elastic and rigid single sections, it being possible for connecting devices once again to be provided for this purpose, as they have been described in the preceding.

Figure 9A:
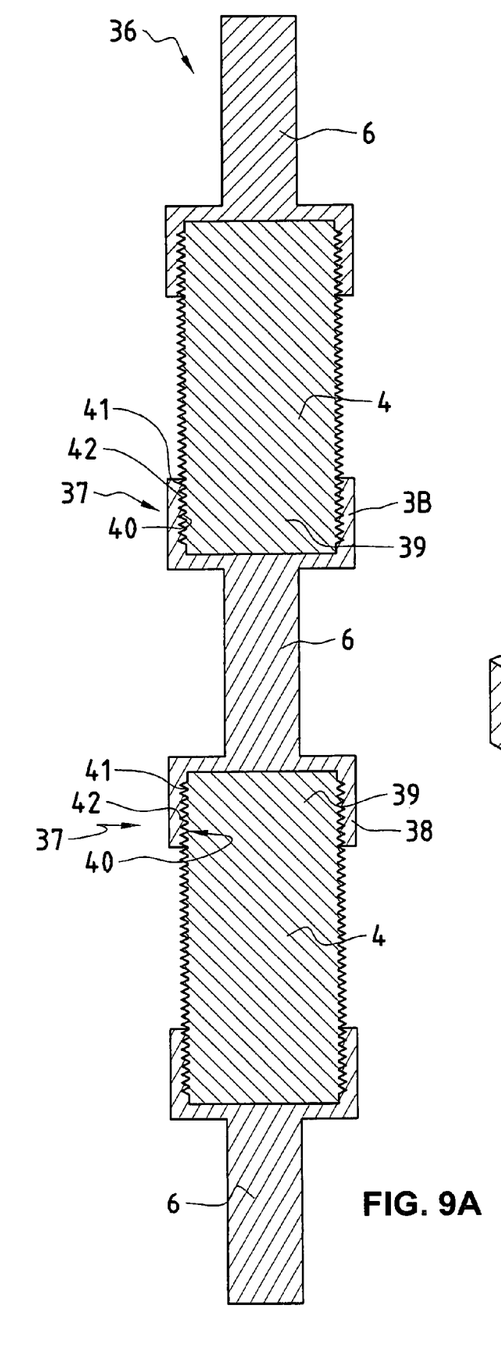
FIGS. 9 to 12 show various possibilities of connecting elastic sections and rigid sections when parts of a connecting element, made up of elastic and rigid sections, are prefabricated.
Figure 9B:
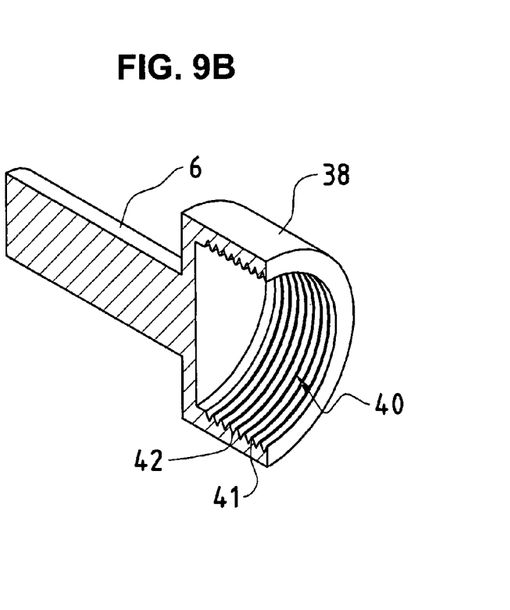

FIGS. 9A and 9B show a first possibility for a connecting device usable for such a prefabricated portion 36 of a connecting element. This portion 36 consists of rigid sections 6 and elastic sections 4, which are connected together via a connecting device 37. For this purpose, formed on the rigid section 6 at the end is a sleeve 38, which is provided with a coaxial bore 39. The walling 40 is provided with encircling ribs 41 and grooves 42, which are aligned transversely to the bore 39. In the production process for such a portion 36, the elastic section 4 is brought into a mold through injection molding or pressure casting, which mold is closed off on both sides with a rigid section. The injected material of the elastic section 4 completely fills the bore 39 of the respective rigid section 6. After the solidification of the material, by means of the ribs 41, which are made as projections in the walling 40 of the bore 39, and grooves 42, one has a firm, form-fitting connection between the respective elastic section 4 and the respective rigid section. In the example shown here, the elastic section between the rigid sections also has a ribbed surface; this surface could also be smooth, however.

Figure 10A:
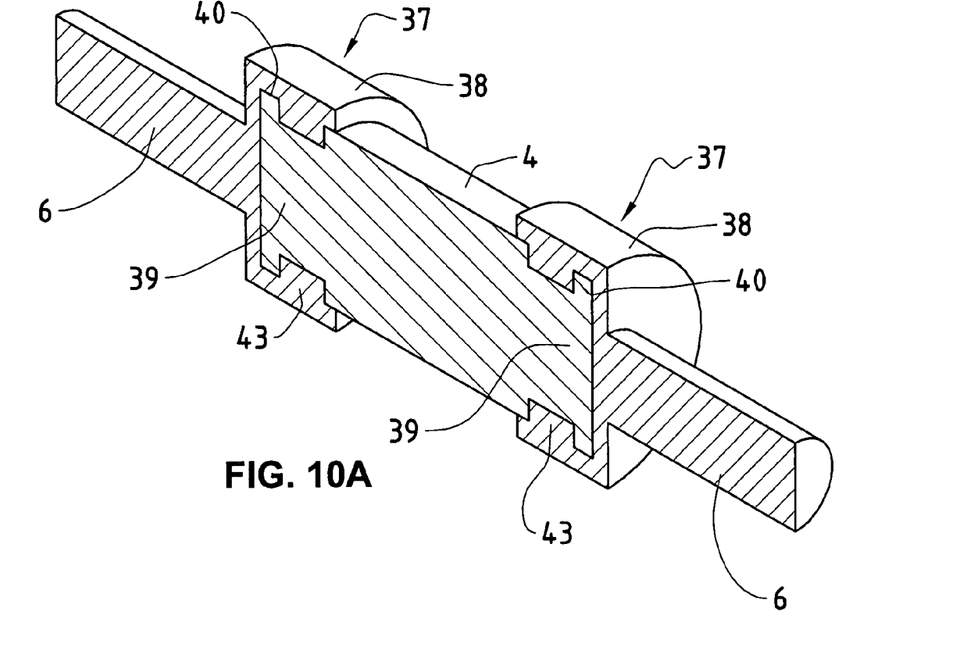
Figure 10B:
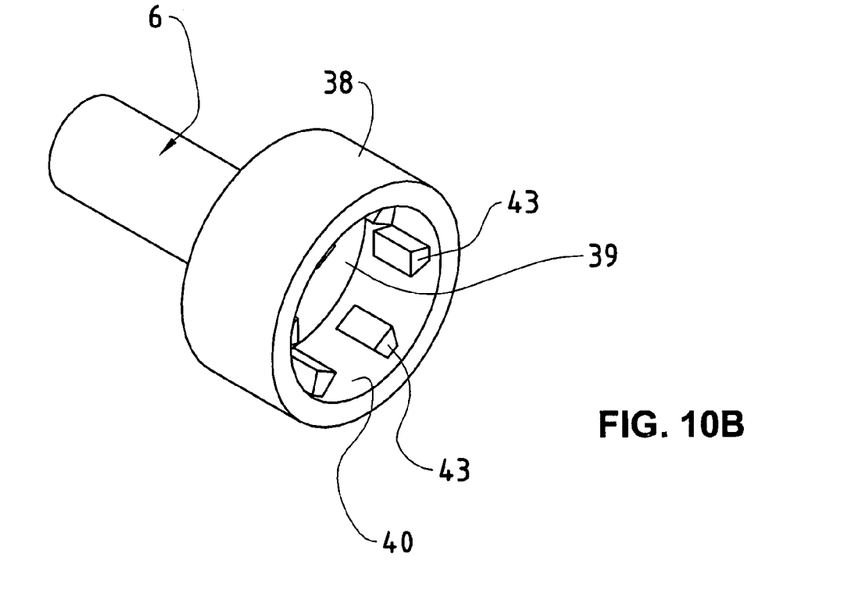

FIGS. 10A and 10B show another embodiment of a connecting device 37 for a prefabricated portion 36. Provided on the rigid section 6 is once again a sleeve 38, which is provided with a bore 39. The walling 40 of the bore 39 is provided with projections which have the form of teeth 43. After the production process, as it is described above, a form-fitting connection is also achieved here between elastic sections 4 and rigid sections 6.

Figure 11A:
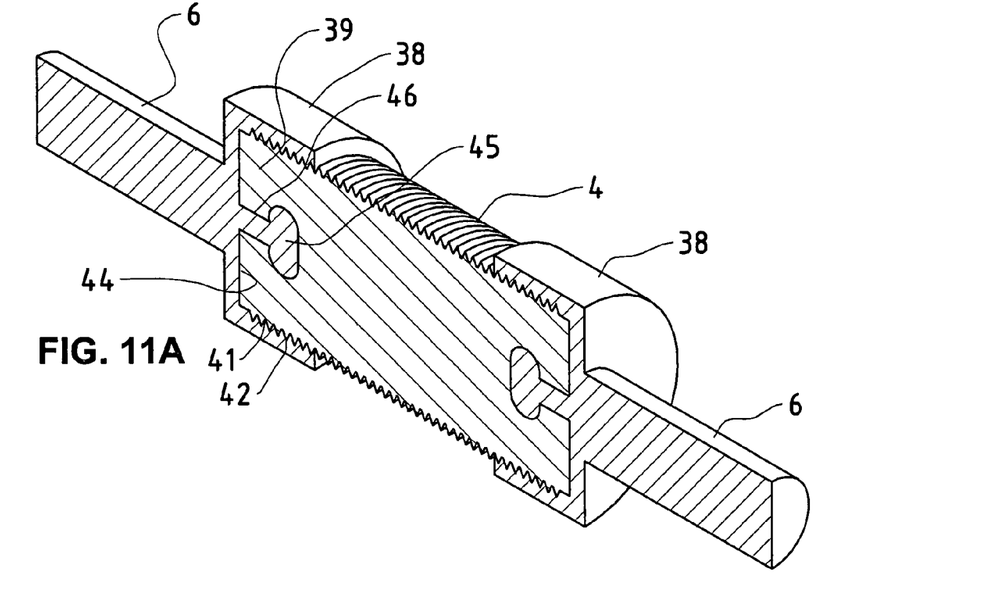
Figure 11B:
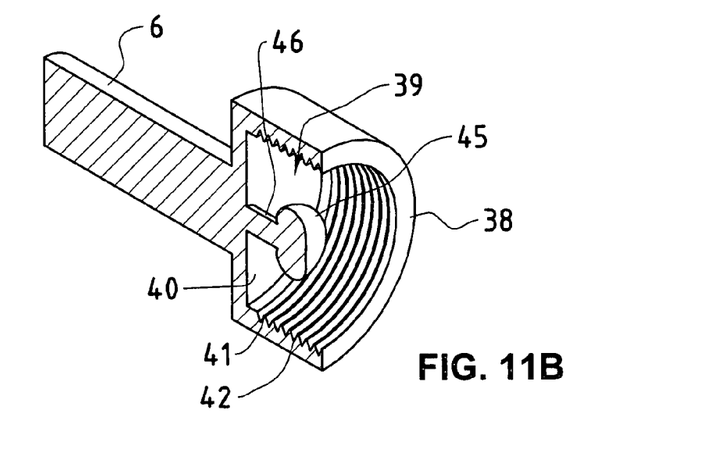

FIGS. 11A and 11B likewise show a form-fitting connection between elastic sections 4 and rigid sections 5, provided here in the bottom 44 of the bore 39 being a bolt 46 formed with a mushroom-shaped swelling 45. Here, too, the walling 40 of the bore 39 is provided with ribs 41 and grooves 42, it being possible, however, to do without these. The elastic section 4 can have a surface here too which is ribbed or smooth.

Figure 12A:
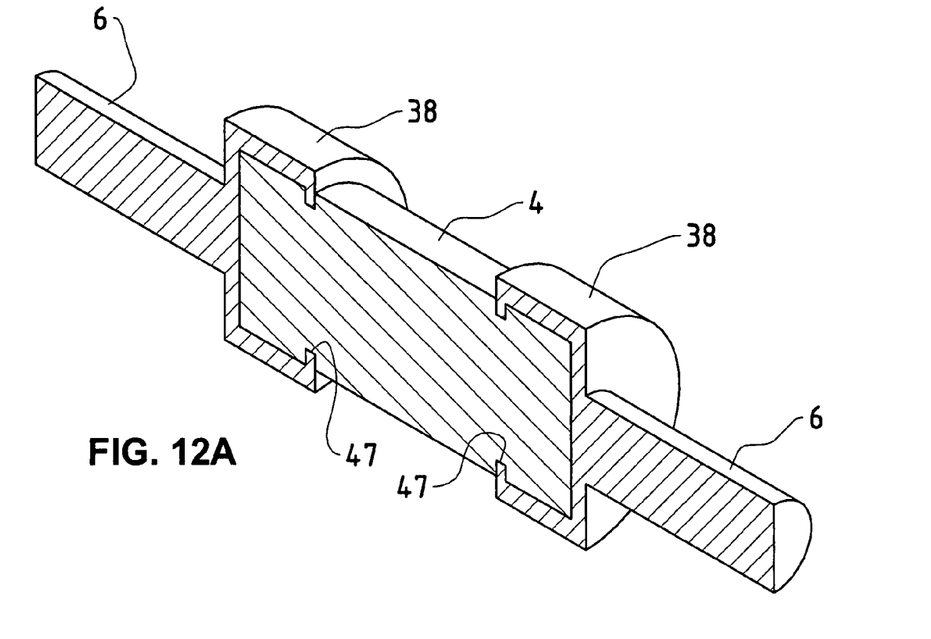
Figure 12B:
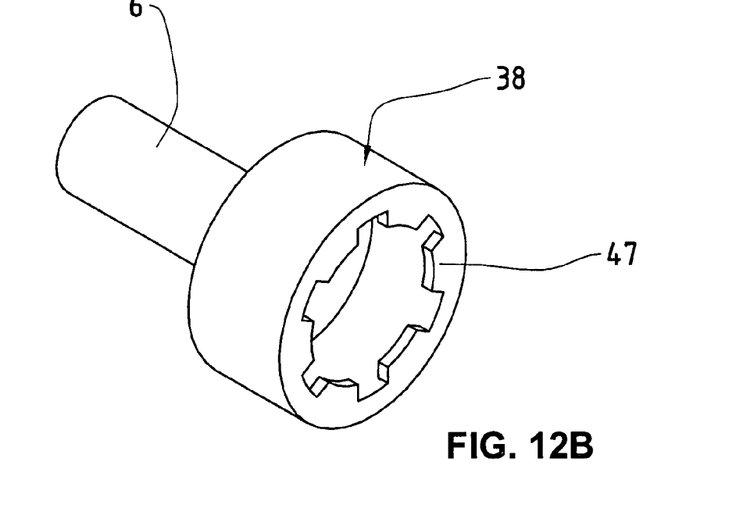

FIGS. 12A and 12B show another form-fitting connection between elastic sections 4 and rigid sections 6, provided on the rim of the sleeve 38 being projections which are designed as a collar 47. This collar 47 can extend over the entire circumference, but it can also be provided with interruptions, as shown here in FIG. 12B.

The rigid sections 6 shown in FIGS. 9 to 12 are provided in each case with a formed sleeve. It is also conceivable that the respective bore is made directly into the body of the rigid section, if the required dimensions allow this.

With this vertebral column implant according to the invention, practically any desired possibilities of combination result, so that a connecting element can be constructed which can be inserted in the corresponding bone screws and which makes possible the desired stabilization in the individual regions of the vertebral column.

The invention claimed is:
1. A vertebral column implant, comprising
a connecting element and a multiplicity of bone screws, the multiplicity of bone screws being screwable into vertebral bodies of the vertebral column and each of the bone screws being provided with a head part for receiving the connecting element, the head parts providing a firm connection between the multiplicity of bone screws and the connecting element,
the connecting element including at least one rigid section and at least one elastic section,
both the at least one rigid section and the at least one elastic section having two ends, respectively, one of the two ends of the at least one rigid section being connectible to one of the two ends of the at least one elastic sections via a connecting device, said connecting device being formed on the one end of the two ends of the at least one rigid section, the connecting device locking the one end of the at least one rigid section to the one end of the at least one elastic section in substantially coaxial alignment and a connection between the one end of the at least one rigid section and the one end of the at least one elastic section being form-fitting, a surface of the at least one elastic section including encircling ribs and grooves, the connecting device being composed of a U-shaped bow made of a rigid material, the U-shaped bow including a bottom and legs, said legs having free ends, the bottom of the bow and along an inner side of the legs having grooves and ribs corresponding to the ribs and grooves of the at least one elastic section, the U-shaped bow being closed on one side by a plate, the plate connecting the U-shaped bow to the one end of the at least one rigid section.

2. The vertebral column implant according to claim 1, wherein the at least one rigid section is made of a titanium alloy.

3. The vertebral column implant according to claim 1, wherein the at least one elastic section is made of a biocompatible synthetic material based on polyurethane.

4. The vertebral column implant according to claim 1, wherein the U-shaped bow when receiving an inserted elastic section, is locked by a locking piece, the locking piece is insertable between the legs of the U-shaped bow and is held via engagement means.

5. The vertebral column implant according to claim 4, wherein the locking piece has, on a side facing the inserted elastic section, ribs and grooves corresponding to the ribs and grooves of the inserted elastic section.

* * * * *